United States Patent [19]
Rubinfeld et al.

[11] Patent Number: 5,824,668
[45] Date of Patent: Oct. 20, 1998

[54] FORMULATION FOR ADMINISTRATION OF STEROID COMPOUNDS

[75] Inventors: Joseph Rubinfeld, Contra Costa County, Calif.; Julius A. Vida, Fairfield County, Conn.; H. Leon Bradlow, Queens County, N.Y.; Elliott L. Fineman, Contra Costa County, Calif.

[73] Assignee: Supergen, Inc., San Ramon, Calif.

[21] Appl. No.: 744,979

[22] Filed: Nov. 7, 1996

Related U.S. Application Data

[60] Provisional application No. 60/006,557 Nov. 13, 1995.

[51] Int. Cl.$^6$ .................................................. A61K 31/56
[52] U.S. Cl. .......................... 514/170; 514/178; 514/814; 514/866; 514/909
[58] Field of Search .................... 514/170, 178, 514/814, 866, 909

[56] References Cited

U.S. PATENT DOCUMENTS

| | | | |
|---|---|---|---|
| 4,024,223 | 5/1977 | Noda et al. | 424/180 |
| 4,228,160 | 10/1980 | Szejtli et al. | 424/180 |
| 4,232,009 | 11/1980 | Hayashi et al. | 424/180 |
| 4,351,846 | 9/1982 | Matsumoto et al. | 424/305 |
| 4,352,793 | 10/1982 | Yamahira et al. | 424/180 |
| 4,383,992 | 5/1983 | Lipari | 424/238 |
| 4,407,795 | 10/1983 | Nicolau et al. | 424/180 |
| 4,424,209 | 1/1984 | Tuttle | 424/180 |
| 4,425,336 | 1/1984 | Tuttle | 424/180 |
| 4,438,106 | 3/1984 | Wagu et al. | 424/180 |
| 4,474,811 | 10/1984 | Masuda et al. | 424/317 |
| 4,478,995 | 10/1984 | Shinoda et al. | 536/46 |
| 4,479,944 | 10/1984 | Hayashi et al. | 424/180 |
| 4,479,966 | 10/1984 | Hayashi et al. | 424/305 |
| 4,497,803 | 2/1985 | Harada et al. | 514/450 |
| 4,499,085 | 2/1985 | Masuda | 514/58 |
| 4,507,289 | 3/1985 | Coleman et al. | 514/170 |
| 4,518,595 | 5/1985 | Coleman et al. | 514/178 |
| 4,524,068 | 6/1985 | Szejtli et al. | 514/58 |
| 4,555,504 | 11/1985 | Jones | 514/26 |
| 4,565,807 | 1/1986 | Uekama et al. | 514/58 |
| 4,575,548 | 3/1986 | Ueda et al. | 536/46 |
| 4,596,795 | 6/1986 | Pitha | 424/238 |
| 4,598,070 | 7/1986 | Ohwaki et al. | 514/58 |
| 4,603,123 | 7/1986 | Chiesi et al. | 514/58 |
| 4,608,366 | 8/1986 | Hasegawa et al. | 514/58 |
| 4,623,641 | 11/1986 | Szejtli et al. | 514/58 |
| 4,659,696 | 4/1987 | Hirai et al. | 514/15 |
| 4,663,316 | 5/1987 | Ninger et al. | 514/99 |
| 4,666,898 | 5/1987 | Coleman et al. | 514/177 |
| 4,675,395 | 6/1987 | Fukazawa et al. | 536/103 |
| 4,727,064 | 2/1988 | Pitha | 514/58 |
| 4,728,509 | 3/1988 | Shimizu et al. | 424/81 |
| 4,728,510 | 3/1988 | Shibanai et al. | 424/94.5 |
| 4,751,095 | 6/1988 | Karl et al. | 426/548 |
| 4,871,726 | 10/1989 | Applezweig et al. | 514/177 |
| 4,920,115 | 4/1990 | Nestler et al. | 514/178 |
| 4,983,586 | 1/1991 | Bodor | 514/58 |
| 5,006,517 | 4/1991 | Bradlow et al. | 514/178 |
| 5,024,998 | 6/1991 | Bodor | 514/58 |

FOREIGN PATENT DOCUMENTS

| | | |
|---|---|---|
| 149220 | 7/1985 | European Pat. Off. . |
| 261891 | 3/1988 | European Pat. Off. . |
| 477107 | 3/1992 | European Pat. Off. . |
| WO 92/04888 | 4/1992 | WIPO . |

OTHER PUBLICATIONS

Brewster, M. et al. "Preparation, Characterization, and Anesthetic Properties of 2–Hydroxypropyl–β–cyclodextrin Complexes of Pregnanolone and Pregnenolone in Rat and Mouse", *J. Pharm. Sciences*, 84:10, 1154–1159 (Oct. 1995).

Shimada, et al., "Studies on Neurosteriods.I.Retention Behavior of Derivatized 17–Oxosteroids Using High–Performance Liquid Chromatography", *J. Liquid Chromatography*, 18:4, 712–723 (1995).

Yen et al., "Prevention of Obesity in A$^{vy}$/a Mice by Dehydroepiandrosterone", *Lipids*, 12(5), 409 (1977).

Coleman, "Diabetes–Obesity Syndromes in Mice", *Diabetes*, 31 (Suppl. 1), 1 (1982).

Coleman et al., "Therapeutic Effects of Dehydroepiandrosterone Metabolites in Diabetes Mutant Mice", *Endocrinology*, 115, 239 (184).

Coleman, Antiobesity Effects of Etiocholanolones in Diabetes (db), Viable Yellow (A$^{vy}$), and Normal Mice *Endocrinology*, 117, 2279 (1985).

Zumoff et al., "A Randomized Double–Blind Crossover Study of the Antiobesity Effects of Etiocholanedione", *Obesity Research*, 2, 13 (1994).

Gardner et al., "Androstane Therapy to Treat Aplastic Anaemia in Adults: An Uncontrolled Pilot Study", *British Journal of Hematology*, 65, 295 (1987).

Kappas et al., "The Pyrogenic Effect of Etiocholanolone (3α–Hydroxyetiocholane–17–One)", *J. Clin. Endocr.*, 16, 948 (1956).

Kappas et al., "Studies on Pyrogenic Steroids in Man", *Tans. Assn. Am. Phys.*, 72, 54 (1959).

Bradlow et al., "Some Aspects of the Dynamics of Oxidation–Reduction of Etiocholanolone–3–$^3$H–$^{14}$C in Man", *J. Clin. Endocr.*, 27, 1203 (1967).

Bekers et al., "Stabilization of Mitomycins on Complexation With Cyclodextrins in Aqueous Acidic Media", *Intl. J. of Pharmaceutics*, 52, 239 (1989).

Primary Examiner—Kimberly Jordan
Attorney, Agent, or Firm—Wilson Sonsini Goodrich & Rosati; Elliott L. Fineman

[57] ABSTRACT

Disclosed are compositions including at least one 5β steroid and an amorphous cyclodextrin. Also disclosed are methods for treating a condition such as obesity, diabetes syndrome, diabetes-associated hypercorticoidism, combinations thereof, and anemic disorders by administering to a mammal in need of such treatment a composition including an obesity-, diabetes-, or anemia antagonistic amount of at least one 5β steroid and an amorphous cyclodextrin. Furthermore, disclosed are methods for treating a subject for a condition that responds to treatment with DHEA by administering to the subject at least one 5β steroid and DHEA in an amount that minimizes the contribution of the DHEA to the production of testosterone and estradiol while maximizing an amount of αET and βET circulating in the subject's blood from an initial dose administered to the subject.

43 Claims, No Drawings

FORMULATION FOR ADMINISTRATION OF STEROID COMPOUNDS

This application claims benefit of U.S. Provisional patent application number Ser. No. 06/006,557, having the same title, filed on Nov. 13, 1995.

FIELD OF THE INVENTION

The present invention relates to improved formulations for the administration of certain steroid and steroid related compounds, which renders them more effective and which also facilitates parenteral administration of these compounds.

BACKGROUND OF THE INVENTION

Steroid compounds are powerful drug substances generally well known in biology, medicine and pharmaceutical sciences. These compounds effect a number of important physiological functions in mammals and in human beings in particular.

Many of the beneficial steroids that are administered therapeutically to patients are insoluble in water. As a result, few of the active steroids can be administered in aqueous solution parenterally. As a result of the insolubility of steroids in aqueous media many of the active steroids are administered in organic solvent vehicles particularly when administered topically and by injection. If injected, steroids are usually administered using a needle into the muscle or intramuscularly (im) or into the layer below the skin or subcutaneously. Steroids injected by both of these routes are absorbed gradually into the blood of the patient. The resulting peak concentration of the drug in the blood is obtained only slowly and the therapeutic effect of the drug may be achieved only gradually and after some delay.

Because of these problems in parenteral administration of steroids, these compounds are usually administered orally especially when chronic administration is required to exert a therapeutic effect. Absorption of the compounds by the oral route however, is limited. In most cases, if taken orally, less than 15 percent of the drug reaches the blood stream. One reason for the low percentage of steroid reaching the blood stream is that much of the drug that is absorbed across the intestinal tract is shunted to the liver where it is deactivated before it can exert its therapeutic effect at the target organ which may be far removed from the liver.

The limitations of steroid absorption by both the oral and parenteral routes have lead researchers to invent and develop new and more powerful versions of the naturally occurring steroids. The resulting compounds exert their desired therapeutic effects at low concentration because they are more powerful than the naturally occurring steroids produced by the body. However, coupled with these powerful therapeutic effects are frequently equally powerful side effects. For example the anti-inflammatory corticosteroid prednisone is effective in reducing the symptoms associated with many auto-immune diseases such as ulcerative colitis, Chrone's disease and rheumatoid arthritis, but this powerful steroid also causes fluid retention and dramatic loss of bone or osteoporosis.

Another result of the limitations of steroid administration is that naturally occurring steroids are not utilized effectively as therapeutics. The use of naturally occurring steroids instead of the more powerful synthetic compounds is highly desirable because the naturally occurring steroids exert their beneficial effects with few if any side effects. Unfortunately, such high levels of naturally occurring steroid administration are required to obtain therapeutic benefit that the cost of such naturally occurring steroid products becomes prohibitive. Thus, the possibility of using naturally occurring steroids administered parenterally as therapeutic agents has been limited heretofore.

Formulations have been proposed in the past to improve the availability of water-insoluble compounds in dosage forms that may be administered parenterally, either intravenously, intra peritoneally, intrathecally or intramuscularly. Of these routes, the first three are the most desirable since the highest concentration of the compound is achieved in the shortest time. Liposomes, small envelopes of fat-like compounds containing an aqueous chamber or chambers within, have been proposed for the parenteral administration of a number of water-insoluble compounds. The water insoluble compound is dissolved in the fat-like compound comprising the envelope of the liposome. Liposomes, however, have the disadvantage of being preferentially removed from the circulation and retained in the liver and spleen. Therefore, unless it is proposed to target the water-insoluble therapeutic compound to these organs liposomes are not desirable. Liposomes also have a number of other disadvantages, including instability when stored for long and short periods of time. Change in the size of the liposome on storage is also a major problem.

Another approach as has been to form a reversible complex between the insoluble drug, such as a steroid, and a carrier molecule. The characteristics of the carrier molecule are such that the carrier molecule and the reversible complex are soluble in water. Among these known carrier molecules are cyclodextrin compounds.

A variety of improvements in the characteristics of pharmaceutical complexes including various cyclodextrins and cyclodextrin derivatives are disclosed in the following U.S. Pat. Nos.: Noda et al., U.S. Pat. No. 4,024,223 methyl salicylate; Szejtli et al U.S. Pat. No. 4,228,160 indomethacin; Hyashi et al., U.S. Pat. No. 4,232,009 ω-halo-PGI$_2$analogs; Matsumoto et al., U.S. Pat. No. 4,351,846 3-hydroxy and 3-oxo prostaglandin analogs; Yamahira et al., U.S. Pat. No. 4,353,793, bencyclane fumarate; Lipari, U.S. Pat. No. 4,383,992 steroids-corticosteroids, androgens, anabolic steroids, estrogens, progestagens complexed with β cyclodextrin, but not substituted amorphous β cyclodextrins; Nicolau, U.S. Pat. No. 4,407,795 P-hexadecylaminobenzoic acid sodium salt; Tuttle, U.S. Pat. No. 4,424,209 3,4-diisobutyryloxy-N-{3-(4-isobuttyryloxyphenyl)-1-methyl-n-propyl]-β-phenethylamine, Tuttle, U.S. Pat. No. 4,425,336, 3,4-dihydroxy-N-[3-(4-hydroxyphenyl)-1-methyl-n-propyl]-β-phenethylamine; Wagu et al., U.S. Pat. No. 4,438,106 fatty acids EPA and DHA; Masuda et al., U.S. Pat. No. 4,474,881 2-(2-fluoro-4-biphenyl)propionic acid or salt; Shinoda et al., U.S. Pat. No. 4,478,995 acid addition salt of (2'-benzyloxycarbonyl)phenyl trans-4-guanidinomehtylcyclo-hexanecaboxylate; Hyashi et al., U.S. Pat. No. 4,479,944 Prostaglandin I$_2$ analog; Hayashi et al., U.S. Pat. No. 4,479,966, 6,9-methano-prostaglandin I$_2$ analogs; Harada et al., U.S. Pat. No. 4,497,803 lankacidin-group antibiotic; Masuda U.S. Pat. No. 4,499,085 prostoglandin analog; Szejtli et al., U.S. Pat. No. 4,524,068 piperonyl butoxide; Jones, U.S. Pat. No. 4,555,504 cardiac glycoside; Uekama et al., U.S. Pat. No. 4,565,807 pirprofen; Ueda et al., U.S. Pat. No. 4,575,548 2-nitroxymethyl-6-chloropyridine; Ohwaki et al., U.S. Pat. No. 4,598,070 tripamide anti-hypertensive; Chiesi et al., U.S. Pat. No. 4,603,123 piroxicam (feldene); Hasegawa et al., U.S. Pat. No. 4,608,366 monobenzoxamine; Hiari et al., U.S. Pat. No. 4,659,696 polypeptide; Szejtili et al., U.S. Pat. No. 4,623, 641 Prostoglandin I$_2$ methyl ester; Ninger et al., U.S. Pat. No. 4,663,316. unsaturated phosphorous containing antibiotics including phosphotrienin; Fukazawa et al., U.S. Pat. No. 4,675,395 hinokitol; Shimizu et al., U.S. Pat. No. 4,728,509 3-amino-7-isopropyl-5-oxo-5H-[1]-benzopyrano[2,3-b]pyridine-3-carboxcylic acid; Shibani et al. U.S. Pat. No. 4,728,510 milk component; and Karl et al., U.S. Pat. No. 4,751,095 aspartame.

Among the above-mentioned patents, several indicate that complexes of cyclodextrin with drug substances improve side effects of the drug substance. Szejtli et al., U.S. Pat. No. 4,228,160 disclosed that the frequency and severity of gastric and duodenal erosion and ulceration in rats caused by indomethecin is improved in an oral formulation of a complex of β-cyclodextrin: indomethacin in a 2:1 ratio, but is not improved and in fact worsens in the same oral formulation of a complex of β-cyclodextrin: indomethacin in a 1:1 ratio.

Shimazu et al., U.S. Pat. No. 4,352,793 discloses that a formulation wherein bencyclane fumarate an anti-convulsive compound and β-cyclodextrin or γ-cyclodextrin yields a complex in which the bencyclane fumarate is an inclusion compound. These complexes, when formulated as a liquid suitable for oral administration were claimed to be less irritating in an isotonic buffered pH 7 solution when administered as drops to the eyes of rabbits, as compared to bencyclane fumarate drops at the same drug concentration. Shimazu et al., also discloses that similar complexes dissolved in rabbit blood in vitro yielded reduced hemolysis as compared to equal concentrations of bencyclane fumarate alone mixed with rabbit blood.

Masuda et al., U.S. Pat. No. 4,478,811 disclose ophthalmic formulations of β- or γ-cyclodextrin complexes of the nonsteroidal anti-inflammatory compound fluoro-bi-phenylacetic acid which are less irritating and painful than the same formulations of fluoro-bi-phenyl acetic acid alone.

Uekama et al., U.S. Pat. No. 4,565,807 discloses complexes of α-, β- and γ- cyclodextrin, piprofen and a pharmaceutically acceptable base. Piprofen is an analgesic and anti-inflammatory compound which is bitter and can cause irritation to the gastrointestinal tract. The complexes disclosed in the patent have improved less bitter taste and are less gastrointestinal irritating than the uncomplexed compound piprofen. No preparations suitable for intravenous injection were disclosed.

Lipari, U.S. Pat. No. 4,383,992 discloses topical and ophthalmic solutions comprising a number of different steroid-related compounds including corticosteroids, androgens, anabolic steroids, estrogens, and progestagens complexed with β cyclodextrin. None of the cyclodextrin compounds disclosed by Lipari are substituted or amorphous cyclodextrins. In addition, none or the steroid related compounds disclosed by Lipari are 5β steroids.

Pitha et al., U.S. Patent No. 4,596,795 discloses complexes containing amorphous hydroxypropyl-β-cyclodextrin and sex hormones, particularly testosterone, progesterone and estradiol as a lyophilized powder in tablet form. These tableted complexes are disclosed as appropriate for administration sublingually or bacilli with absorption occurring across the corresponding mucosal membrane. None is administered in solution parenterally. In addition none of the steroid related compounds disclosed by Pitha et al are 5β steroids.

Pitha et al., U.S. Pat. No. 4,727,064 discloses complexes containing water soluble amorphous substituted cyclodextrin mixtures and drugs with substantially low water solubility which may be lyophilized and the lyophilized powder formed into dosage forms suitable for absorption transmucocele across the oral, buccal or rectal mucosa. The solutions of amorphous water soluble cyclodextrin alone and not in a complex with a drug substance are disclosed as nonirritating topically, and having low toxicity, both systemic and local, when applied parenterally. These solutions of substituted cyclodextrin alone were tested and shown to be non-lethal when substantial amounts of the cyclodextrin solution were administered intra peritoneally in mice. There was no disclosure indicating whether the solutions cause elevated temperature in test subjects. This phenomenon called the pyrogenic effect is highly objectionable in parenteral dosage forms. A number of categories of drugs are disclosed in Pitha et al. '067 for complex with cyclodextrin derivatives and include inter alia vitamins, salts of retinoid acid, spironolactone, antiviral agents, diuretics, anticoagulants, anticonvulsant and anti-inflammatory agents. Significantly, Pitha et al. '067 while disclosing that aqueous solutions of 50% cyclodextrin may be used for the purpose of determining solubility of drugs in such solutions does not indicate that such solutions are suitable for intravenous administration. No attempt is made to qualify the solution as to its pyrogenicity. The claimed compositions of matter in the reference contain only cyclodextrin and drug. Liquid or semi-liquid compositions of matter, which are claimed in the reference, appear to be made of cyclodextrins with higher degrees of substitution with hydroxy propyl groups. These cyclodextrins are themselves semi-solid or liquids according to the reference. Thus no aqueous formulations of water, cyclodextrin and drug are disclosed or claimed as suitable for parenteral administration in the reference.

Bekers, O., et al., "Stabilization of mitomycins on complex with cyclodextrins in aqueous acidic media" International Journal of Pharmaceutics, 53, 239–248 (1989) describes the investigation of stabilization of mytomycin-C and several related mitomycins by formation of a complex with cyclodextrin. The authors indicate that at the pH ranges studied α- and β- cyclodextrin as well as heptakis-(2,6,-di-O-methyl)-β- cyclodextrin and dimethyl-β- cyclodextrin, have no influence on stabilization of mitomycin-C pH degradation. γ-cyclodextrin is reported as having measurable stabilizing effect on mitomycin in acidic media at pH above 1.

Bodor, U.S. Pat. No. 5,024,998 and Bodor, U.S. Pat. No. 4,983,586 disclose a series of compositions comprising complexes of hydroxypropyl-β-cyclodextrin (HPCD) complexed to a difficult to solubilize drug, or HPCD complexed to a drug which has first been complexed to a specific class of drug carriers characterized as redox drug carriers. The complex of drug and redox carrier is itself difficult to solubilize and is highly lipophilic due to the presence of pyridine derivatives as part of the redox carrier complex. Bodor '998 and '586 further claim that a solution of 20 to 50% hydroxypropyl-β-cyclodextrin and lipophilic drug-redox carrier complex, or 20 to 50% hydroxypropyl-β-cyclodextrin and lipophilic and/or water labile drug is useful in a method of "decreasing the incidence of precipitation of a lipophilic and/or water labile drug occurring at or near the injection site and/or in the lungs or other organs following parenteral administration."

Significantly the Bodor references attribute the precipitation and organ deposition problems associated with parenteral administration of lipophilic drugs to the effects of organic solvents used to solubilized the drug in the parenteral vehicle. The Bodor references additionally state that drugs which are particularly useful in the parenteral composition and methods disclosed therein are those which are relatively insoluble in water but whose water solubility can be substantially improved by formulation with 20 to 50% of the selected cyclodextrin, e.g., HPCD, in water. Significantly no part of Bodor addresses the pyrogenic load on the cyclodextrin or the issue of the pyrogenic effect of the composition when injected parenterally. Thus it is quite clear that the Bodor references are directed to prevention of the phenomenon of precipitation of insoluble drugs and insoluble drug-carrier complexes.

There are a number of disclosures relating to the 5β steroids used in the formulations disclosed herein below according to the invention. Yen et al., Lipids, 12, 409 (1977) disclosed that dehydroepiandrosterone DHEA (a 5 α steroid) administered by a variety of routes decreased the rate of weight gain in a strain of genetically obese mice. DHEA treatment markedly reduced the development of diabetes in both genetically obese and diabetic mice and maximal benefit was observed when DHEA was ingested according to Coleman et al., *Diabetes*, 31:80 (1982). Coleman et al., *Endocrinology*, 115, 239 (1984) showed that α ET and β ET reduce blood sugar, increased plasma insulin concentrations and provided a protective effect on the pancreas as demonstrated by increased granulation of islet P cells. Moreover, α ET and β ET but not androsterone or epiandrosterone, were four times more effective than DHEA in preventing development of diabetes in C57BL/KsJ-db/db diabetic mice. Coleman et al., U.S. Pat. No. 4,518,595 showed that oral administration of DHEA restored hyperglycemia to normal levels and improved glucose tolerance even in severely diabetic mammals. In U.S. Pat. No. 4,507,289 Coleman taught the use of α ET and β ET and an estrogen for the treatment of diabetes, obesity syndromes and associated hypercorticoidism.

Coleman, *Endocrinology*, 117, 2279 (1985) disclosed that α ET and β ET when supplied in the diet have anti-obesity properties, and can prevent and arrest the development of obesity, and facilitate weight reduction after obesity in diabetic genetically obese mice. U.S. Pat. No. 4,666,898 to Coleman and Applezweig disclosed the use of Etiocholanolones in the treatment of obesity, diabetes and other symptoms of hypercorticoidism. B. Zumoff et al., *Obesity Research*, 2, 13 (1994) disclosed that ED orally administered at a dose of four grams per day yielded significant fat loss in human obese subjects. In a 20 week randomized double-blind cross over study, 14 subjects lost significantly more weight and body fat during treatment with oral ED than during placebo administration. Mean weight loss during ED administration was 2.8±5.5 kilograms which was equivalent to 0.5±0.91 kilograms per week per 100 kilograms of body fat. Densitometric measurement of body fat content showed that the mean weight loss coincided almost exactly with the mean decrease in body fat content. Over the 10-week period of ED administration, the mean fat loss was about 5% of the initial body fat content. There were no significant subjective or objective side effects of ED administration. In all of the foregoing references, the 5β steroids or DHEA is administered orally with or without food.

U.S. Pat. No. 5,006,517 to Bradlow, et al., discloses that Prader-Willi Syndrome a congenital disease caused by a chromosomal defect may be treated by administering etiocholanolone or etiocholanolondione to individuals suffering from the syndrome resulting in either weight loss or a decrease in the rate of weight gain in the treated individuals.

Gardner and Juneja, Brit. J. Hemat., 65,295–300 (1987) treated aplastic anemia patients with either α- and/or β ET in an uncontrolled pilot study. Of 43 treated patients, 17 had hematologic responses lasting longer than six months including normalization of hemoglobin level for long periods of time which persisted after α-ET was discontinued. Kappas et al., J. Clin Endocr., 16, 284 (1956); Kappas et al., Trans. Assn. Am. Phys., 72,54 (1959) showed that α-ET engendered acute pyrogenic reactions in man when administered by intramuscular injection. This observation lead Gardner and Juneja to concomitantly administer prednisolone along with the intramuscular therapeutic injections of α-ET to prevent development of fever and to alleviate local irritation at the injection sites. The α-ET and β-ET as described below, were administered in a sterile polypropylene vehicle by im route because the 5β steroids are notoriously insoluble in aqueous solutions and therefore cannot be administered by intravenous route.

Gardner and Juneja also observed that three patients who did not respond to α ET had a hematologic recovery when treated with β-ET. Significantly, β-ET evidenced little pyrogenic effect and minimal prednisolone doses of 10 mg were sufficient to suppress any local irritation.

The metabolism and elimination routes of the 5β steroids have been investigated by several groups. Administration of α ET and β ET by parenteral routes resulted in the recovery of almost exclusively α ET conjugates in the urine, Kappas et al., J. Clin Endocr., 16, 284 (1956). In addition Zumoffet al., have shown that β ET or ED when administered to a patient is quickly converted almost exclusively to α ET in the serum of normal and obese subjects (unpublished data). Bradlow et al., J. Clin Endocr. 27,1203–1207 (1967) found that based on isotopic ratio studies, the C3 position of a portion of α ET administered IV to human subjects was rapidly oxidized and re-reduced.

Appelzweig et al., U.S. Pat. No. 4,871,726 disclosed methods and compositions for inducing increased blood levels of α-ET in the body of a mammal by administration of ED, showing that both α ET and β ET administered either orally or parenterally are rapidly oxidized at the C-3 position to form etiocholandione (ED). Furthermore they disclose that ED can serve as a source of circulating blood levels of free α ET, By administering ED, high levels of α ET can be achieved in the serum. In effect ED can serve as a prodrug for α ET according to Appelzweig et al.

While several of the 5β steroids are known to be active in control of obesity and associated diabetic and/or hyper cortical syndrome, the compounds are effective for treatment of these conditions when they are administered orally. By the oral route, the absorption of the 5p steroids is only 5 to 15% as measured by blood levels using various assays. Thus a large portion of the administered drug is never absorbed into the blood stream and the greatest part of the drug that is administered is eliminated in the feces.

To achieve high serum concentrations of a drug, it is more efficient to administer drugs parenterally, preferably by the intravenous (iv) route. However, it has been observed that the 5β steroids do not appear to exert any of their anti-obesity, anti-diabetic or anti-hypercortical activities when administered intramuscularly (im). Furthermore the im route of administration engenders pyrogenic reactions with some of the 5β steroids as described above in Kappas et al. Thus, it would be desirable to have a formulation that would allow parenteral administration of the 5β steroids, preferably by the intravenous (iv) route and which would preserve the antiobesity, anti-diabetic and anti-hypercortical activities of these compounds.

A further long-felt need in the administration of these 5β steroid drugs is to obtain a high serum concentration of the drug without resorting to the intramuscular (im) route of administration which causes local irritation and, at least in the case of α-ET pyrogenic reaction and notable patient discomfort. Furthermore, in that the evidence of Gardner and Juneja implies that pyrogenic reaction associated with im administration is not required to obtain the hematologic activity of the 5β steroids, especially β-ET, it would be desirable to obtain a formulation of the 5β steroids compatible with aqueous iv solutions to maximize the serum concentration of the 5 β steroids. Considerable saving in the cost of active drug substance for a given response could be achieved thereby.

In addition to the advantages of higher serum concentration of drug and drug precursors afforded by a practical aqueous-compatible formulation of α ET and ED respectively, it would be of considerable advantage to provide an aqueous compatible formulation of the drug and prodrug which further includes an amount of β ET which would be clinically effective especially in anemia patients who respond hematologically to β ET but who do not respond to α ET.

The steroid dehydroepiandrosterone (3-β-hydroxy-androst-5-en-17-one, DHEA) and its sulfate derivatives are major steroid adrenal secretory products in humans. DHEA is metabolized to testosterone (17-β-hydroxy-androst-4-en-3-one) and estradiol (estra-1,3,5 (10)-triene-3, 17-diol), two major sex hormones in humans. Other metabolites of DHEA include α ET and β-ET. They were considered to be inert metabolic end products which were merely conjugated as glucuronides or sulfates and excreted into the urine. α ET is a major metabolite of DHEA, and in normal individuals, is excreted in the urine in amounts of about 3–5 mg per day, whereas β ET is a minor metabolite in man.

DHEA has been shown to be effective in controlling diabetes and obesity in rats and mice by Coleman; however in human usage for a number of different inflammatory conditions including the treatment of Lupus Erythematosus, DHEA has demonstrated a number of undesirable side effects. In particular, in female patients, who are the most frequent sufferers of lupus erythematosus, DHEA causes severe acne and may also cause masculinizing effects, particularly hirsutism, the production of facial and body hair.

One of the advantages that may be obtained through the present invention is to reduce the amount of DHEA administered to a patient when administered in an iv formulation. The administration of DHEA by the iv route is advantageous in itself in that the circulating concentrations of the drug can be precisely monitored. If orally administered, the amount of DHEA absorbed through the alimentary tract and reaching the blood stream may vary substantially depending upon the amount if food and liquid the subject has consumed. Furthermore since many inflammatory processes including Chrone's disease and ulcerative colitis affect the intestines and bowel, the absorption of a drug from this area of the body may vary considerably if orally administered. Thus, iv administration may be particularly important for DHEA.

In particular it is believed that some of the salutary effects of DHEA, particularly those relating to inflammatory and autoimmune processes may be preserved while the side effects are eliminated if reduced amounts of DHEA are administered by the parenteral route, especially the iv route. In addition, it is believed that the salutary effects of DHEA on inflammatory and autoimune disease, diabetes and obesity may by preserved even at low concentrations if DHEA is co-administered with one or more of the 5β steroids parenterally. The parenteral administration of DHEA with one or more of the 5β steroids is facilitated in the formulation according to the invention.

SUMMARY AND OBJECTS OF THE INVENTION

It is an object of the invention to provide improved formulations of the 5β steroids suitable for parenteral administration.

It is a further object of the invention to provide improved formulations of the 5β steroids wherein the formulation is a sterile aqueous solution suitable for parenteral administration.

It is yet a further object of the invention to provide improved formulations of the 5β steroids wherein the formulation is a sterile aqueous solution suitable for parenteral administration and is not pyrogenic.

It is a still further object of the invention to provide improved formulations of the 5β steroids wherein the formulation is non-pyrogenic and contains one or more of the 5β steroids.

It is yet still a further object of the invention to provide improved formulations of the 5β steroids wherein the formulation is non- pyrogenic and contains one or more of the 5β steroids and DHEA.

Another object of the invention is to provide methods for treating a subject for a condition which responds to treatment with the 5β steroids by administering to the subject an improved formulation of the 5β steroids suitable for parenteral administration. Among these conditions may be obesity, diabetes syndrome, diabetes-associated hypercorticoidism or combinations thereof, anemic disorders including but not limited to aplastic anemia and anemia associated with renal failure or chemotherapy-induced or radiation-induced anemia or neutropenia, autoimmune or inflammatory disorders such as lupus erythematosus.

It is a further object of the invention to provide a method for treating a subject for a condition which responds to treatment with DHEA using a reduced amount of DHEA by administering to the subject at least one 5β steroid and a reduced amount of DHEA. Among these conditions are those listed above.

Yet a still further object of the invention is to provide a method for treating a subject for a condition which responds to treatment with DHEA using a reduced amount of DHEA by administering to the subject at least one 5β steroid and a reduced amount of DHEA in a formulation including an amorphous cyclodextrin wherein the formulation is suitable for parenteral administration. Among these conditions are those listed above.

Another object of the invention is to provide a method of treating a subject for a condition which responds to treatment with the 5β steroids by administering to the subject an improved formulation of the 5β steroids suitable for parenteral administration which is non-pyrogenic. Among these conditions are those listed above.

DETAILED DESCRIPTION OF THE INVENTION

By 5β steroid is meant α ET, β ET, and ED. In addition certain alkylated derivatives of these 5β steroids are also included in this definition. For example 16- alkylated 5β androstan-3-ol-17-one and 16-alkylated 5β androstan-3, 7-diol-17-one which are disclosed in U.S. Pat. No. 4,602,008, herein incorporated by reference, have been shown to be biologically effective as anti-diabetic, anti-obesity and erythropoietic agents in mammals. These compounds may be esterified at the 3 or 7 positions of the steroid ring structure by conventional means. Also included in the definition is 5-β-androstane -3,17-diol or etiocholandiol (herein after Ediol.) α ET, β ET, Ediol and ED are all commercially available compounds (Research Plus. Inc, POB 324. Bayonne, N.J. 07002 USA).

In addition other diols of the 17 keto 5-β steroids are commercially available and may be used in the invention and may be esterified at the carbon at which the —OH moiety is attached. Thus, for example 5β-androstan-3α, 11α-diol-17-one, 5β-androstan-3β, 11β-diol-17-one, and 5β-androstan-3α, 11β-diol-17-one, 5β-androstane-11α-ol-3, 17-dione, 5β-androstane -11β-ol-3, 17-dione, 5β-androstane-3α, 16α-diol-17-one are commercially available (Research Plus. Inc, POB 324. Bayonne, N.J. 07002 USA) and may be esterified at the 11 or 16 positions, as the case may be, by conventional means to produce the organic acid derivative of the 5β steroids.

By cyclodextrin is meant α-, β-, or γ- cyclodextrin. Cyclodextrins are described in detail in Pitha et al., U.S. Pat. No. 4,727,064 which is incorporated herein by reference. Cyclodextrins are cyclic oligomers of glucose; these compounds form inclusion complexes with any drug whose molecule can fit into the lipophile-seeking cavities of the cyclodextrin molecule.

By amorphous cyclodextrin is meant non-crystalline mixtures of cyclodextrins wherein the mixture is prepared from α-, β-, or γ- cyclodextrin . In general the amorphous cyclodextrin is prepared by non-selective additions, especially alkylation of the desired cyclodextrin species. Reactions are carried out to yield mixtures containing a plurality of components thereby preventing crystallization of the cyclodextrin. Various alkylated and hydroxyalkyl-cyclodextrins can be made and of course will vary, depending upon the starting species of cyclodextrin and the addition agent used. Among the amorphous cyclodextrins suitable for compositions according to the invention are hydroxypropyl, hydroxyethyl, glucosyl, maltosyl and maltotriosyl derivatives of β-cyclodextrin, carboxyamidomethyl-β-cyclodextrin, carboxymethyl-β-cyclodextrin, hydroxypropyl-β-cyclodextrin and diethylamino-β-cyclodextrin. In the compositions according to the invention hydroxy-β-cyclodextrin is preferred. The substituted γ-cyclodextrins may also be suitable, including hydroxypropyl, hydroxyethyl, glucosyl, maltosyl and maltotriosyl derivatives of γ-cyclodextrin.

The cyclodextrin of the compositions according to the invention may be α-, β-, or γ- cyclodextrin. α-cyclodextrin contains six glucopyranose units; β-cyclodextrin contains seven glucopyranose units; and γ-cyclodextrin contains eight glucopyranose units. The molecule is believed to form a truncated cone having a core opening of 4.7–5.3 Å, 6.0–6.5 Å and 7.5–8.3 Å in α-, β-, or γ- cyclodextrin respectively. The composition according to the invention may comprise a mixture of two or more of the α-, β-, or γ- cyclodextrins. Usually, however the composition according to the invention will comprise only one of the α-, β-, or γ- cyclodextrins. The particular α-, β-, or γ- cyclodextrin to be used with the particular 5β steroid compound to form the compositions according to the invention may be selected based on the known size of the molecule of the 5β steroid compound and the relative size of the cavity of the cyclodextrin compound. Generally if the molecule of the 5β steroid compound is relatively large, a cyclodextrin having a larger cavity is used to make the composition according to the invention. Furthermore, if the 5β steroid compound is administered with an excipient it may be desirable to use a cyclodextrin compound having a larger cavity in the composition according to the invention.

The unmodified α-, β-, or γ- cyclodextrins are less preferred in the compositions according to the invention because the unmodified forms tend to crystallize and are relatively less soluble in aqueous solutions. More preferred for the compositions according to the invention are the α-, β-, and γ- cyclodextrins that are chemically modified or substituted. Chemical substitution at the 2,3 and 6 hydroxyl groups of the glucopyranose units of the cyclodextrin rings yields increases in solubility of the cyclodextrin compound.

Most preferred cyclodextrins in the compositions according to the invention are amorphous cyclodextrin compounds. By amorphous cyclodextrin is meant non-crystalline mixtures of cyclodextrins wherein the mixture is prepared from α-, β-, or γ- cyclodextrin. In general, the amorphous cyclodextrin is prepared by non-selective alkylation of the desired cyclodextrin species. Suitable alkylation agents for this purpose include but are not limited to propylene oxide, glycidol, iodoacetamide, chloroacetate, and 2- diethylaminoethlychloride. Reactions are carried out to yield mixtures containing a plurality of components thereby preventing crystallization of the cyclodextrin. Various alkylated cyclodextrins can be made and of course will vary, depending upon the starting species of cyclodextrin and the alkylating agent used. Among the amorphous cyclodextrins suitable for compositions according to the invention are hydroxypropyl, hydroxyethyl, glucosyl, maltosyl and maltotriosyl derivatives of β-cyclodextrin, carboxyamidomethyl-β-cyclodextrin, carboxymethyl-β-cyclodextrin, hydroxypropyl-β-cyclodextrin and diethylamino-β-cyclodextrin. In the compositions according to the invention hydroxypropyl-β-cyclodextrin is preferred although the α- or γ- analogs may also be suitable. The particular alkylated α-, β-, or γ- cyclodextrin to be used with the particular 5β steroid compound to form the compositions according to the invention will be selected based on the size of the molecule of the 5β steroid compound and the relative size of the cavity of the cyclodextrin compound. As with the unsubstituted cyclodextrins mentioned above, it may be advantageous to use alkylated cyclodextrin having a larger cavity when the composition according to the invention also includes an excipient. The use of a particular α-, β-, or γ-cyclodextrin with a particular 5β steroid compound or 5β steroid compound and excipient in the compositions according to the invention may of course be optimized based on the effectiveness in of maintaining the 5β steroid or mixture there of with or without DHEA in solution.

As mentioned above, the compositions of matter of the invention comprise an aqueous preparation of preferably substituted amorphous cyclodextrin and one or more 5β steroids. The relative amounts of 5β steroid compound and cyclodextrin will vary depending upon the relative amount of each of the 5β steroid compounds and the effect of the cyclodextrin on the compound. In general, the ratio of the weight of 5β steroid compound to the weight of cyclodextrin compound will be in a range between 1:1 and 1:5000. Within this range, the circulating availability of the 5β steroid will be significantly increased when the ratio of the weight of 5β steroid to the weight of cyclodextrin compound is in a range between the concentration at which the 5β steroid will not go into solution at the particular amorphous cyclodextrin concentration and 1:2000. A weight to weight ratio in a range of 1:5 to 1:200 and more preferably in a range of 1:5 to 1:50 of 5β steroid compound to cyclodextrin are believed to be the most effective for increased circulating availability of the 5β steroid. For example, ED in a ratio of between 1:10 and 1:300 (drug: amorphous cyclodextrin, wt:wt), and a final concentration of the injection solution of 40 mg/ml of ED is expected to significantly increase circulating concentration of ED as compared to intramuscularly injected ED in a polypropylene vehicle.

Thus α ET, β ET, ED, Ediol or DHEA each individually or in a mixture of two or more may be added to the cyclodextrin solution to form a complex of each compound individually or in a mixture of two or more of these compounds.

Importantly, if the aqueous solution comprising the DHEA and /or 5β steroid and amorphous cyclodextrin is to be administered parenterally, especially via the iv route, the amorphous cyclodextrin will be substantially free of pyrogenic contaminants. Amorphous hydroxypropyl-β-cyclodextrin maybe purchased from a number of vendors including Amaizo, Inc. (Hammond Ind., USA) under the tradename Encapsin. In addition, other forms of amorphous cyclodextrin having different degrees of substitution or glucose residue number are available commercially. A method for the production of hydroxypropyl-β- cyclodextrin is disclosed in Pitha et al., U.S. Pat. No. 4, 727,064 which is incorporated herein by reference.

To produce the formulations according to the invention, a pre-weighed amount of hydroxypropyl-β-cyclodextrin compound, which is substantially pyrogen free is placed in a suitable depyrogenated sterile container. Methods for depyrogenation of containers and closure components are well known to those skilled in the art and are fully described in the United States Pharmacopeia 23 (United States Pharmacopeial Convention, Rockville, Md. USA). Generally, depyrogenation is accomplished by exposing the objects to be depyrogenated to temperatures above 400° C. for a period of time sufficient to fully incinerate any organic matter. As measured in U.S.P. Bacterial Endotoxin Units, the formulation will contain no more than 10 Bacterial Endotoxin Units per gram of amorphous cyclodextrin. By substantially pyrogen free is meant that the hydroxypropyl-β-cyclodextrin contains less than 10 U.S.P. bacterial endotoxin units per gram using the U.S.P. method. Preferably, the hydroxypropyl-β-cyclodextrin will contain between 0.1 and 5 U.S.P. bacterial endotoxin units per mg, under conditions specified in the United States Pharmacopeia 23.

Sufficient sterile water for injection is added to the substantially pyrogen free amorphous cyclodextrin until the desired concentration of hydroxypropyl-β-cyclodextrin is in solution. To this solution a pre-weighed amount of the 5β steroid is added with agitation and with additional standing if necessary until it dissolves.

The solution is then filtered through a sterile 0.2 micron filter into a sterile holding vessel and is subsequently filled in sterile depyrogenated vials and is capped. For products that will be stored for long periods of time, a pharmaceutically acceptable preservative may be added to the solution of 5β steroid and hydroxypropyl-β-cyclodextrin prior to filtration, filling and capping or alternatively, may be added sterilely after filtration.

In the formulations according to the invention, DHEA alone or together with one or more of the 5β steroids may be used. In particular the formulation including DHEA and ED or DHEA and αET and βET or DHEA, ED, αET and βET are desirable. This is particularly desirable in relation to obesity control and inflammatory disease control. It is clear that DHEA is metabolically transformed into the primary male and female sex steroid hormones, testosterone and estradiol respectively, and is ultimately metabolized to α ET and β ET. By reducing the amount of DHEA to an amount which contributes in only a small way to the production of the sex steroids testosterone and estradiol, while at the same time maximizing the amount of α ET and βET circulating in the blood from the initial dose administered to a subject, it is believed that enhancement of the desirable obesity control, hematopoiesis, and anti-inflammatory effects may be achieved while, at the same time, the dermatologic and virilizing side effects of DHEA are minimized to an acceptable degree, if not eliminated.

The invention will be better understood from the following examples which are intended to be merely illustrative of the invention and are not intended to be limiting.

EXAMPLES

Example I 12 milligrams (mg) of Etiocholandione (Steraloids, Inc. New Hampshire) was stirred and shaken with 0.5 ml of water in a test tube. Appreciable quantities of compound remained out of solution after 5 minutes accumulating as white crystals at the bottom of the test tube.

A 50% solution of hydroxypropyl-β-cyclodextrin was prepared as follows. 5 grams of pyrogen free hydroxypropyl-β-cyclodextrin (sold under the trade name Encapsin, Amaizo, Inc., Hammond, Ind., USA) was weighed on an analytical scale and placed in a graduated cylinder. Water was added with shaking until the volume reached 10 ml.

0.5 ml of the 50% solution of hydroxypropyl-β-cyclodextrin was added to the 0.5 ml of water containing 12 mg of Etiocholandione with additional shaking. A clear solution was obtained. Thus, 12 mg ED was effectively solubilized in 1 ml of 25% solution of hydroxypropyl-β-cyclodextrin.

Example II

The previous experiment was repeated using a 50% solution of hydroxypropyl-β-cyclodextrin prepared as in Example 1. 50 mg of Etiocholandione was weighed and placed in a test tube. 2 ml of the 50% solution of hydroxypropyl-β-cyclodextrin was added to the test tube with shaking. Within one minute, the Etiocholandione dissolved, leaving a clear solution with no accumulation of crystals. Thus, 25 mg was effectively solubilized in 1 ml of 50% solution of hydroxypropyl-β-cyclodextrin.

Example III 4 grams of hydroxypropyl-β-cyclodextrin was dissolved in 7 ml of distilled water to a total volume of 10 ml. Each ml of stock solution contained 0.4 g of solution hydroxypropyl-β-cyclodextrin. 20 mg of 3-β-hydroxy androstan-17-one (β-etiocholanolone) was shaken with 1 ml of the freshly prepared stock solution. Partial dissolution took place immediately and after sitting at room temperature with occasional shaking for 6 hours complete dissolution took place.

Example IV

The same experiment as in example III was performed except that 40 mg of β-etiocholanolone was added to the stock solution of hydroxypropyl-β-cyclodextrin. After standing for 24 hr, a complete dissolution had occurred.

Example V

The same experiment as in example III was performed except that 20 mg of Etiocholandione was added to the stock solution of hydroxypropyl-β-cyclodextrin. Complete dissolution occurred within 6 hours.

Example VI

The same experiment as in example V was performed except that 40 mg of Etiocholandione was added to the stock solution of hydroxypropyl-β-cyclodextrin. Complete dissolution occurred within 24 hours.

Example VII

The same experiment as in Example V was performed except 80 mg or 250 mg ED was added to the stock solution. In neither case did the ED completely dissolve.

Example VII

The optical density (OD) of the ET and ED dissolved in hydroxypropyl-β-cyclodextrin solutions was determined at 400 NM against a blank control containing water and set at an OD of 0.0. The dissolved solutions of ET and ED had OD readings of 0.12 whereas the hydroxypropyl-β-cyclodextrin solution containing 80 mg of ED gave an OD of 1.2 at 499 NM.

Example VIII

To make a formulation containing α ET and ED, the stock solution of hydroxypropyl-β-cyclodextrin in prepared as in Example III. 20 mg of α ET and 20 mg of ED will be added to 1 ml of the solution with agitation. An aqueous solution containing 40 mg of the two 5 β steriods and no precipitate is present after standing for 24 hours.

Example IX

To make a formulation containing β ET and ED, the stock solution of hydroxypropyl-β-cyclodextrin in prepared as in Example III. 20 mg of β ET and 20 mg of ED is added to 1 ml of the solution with agitation. An aqueous solution containing 40 mg of the two 5 β steriods and no precipitate is present after standing for 24 hours.

Example X

To make a formulation containing α ET, β ET and ED, the stock solution of hydroxypropyl-β-cyclodextrin is prepared as in Example III. 15 mg of α ET, 15 mg β ET and 15 mg of ED will be added to 1 ml of the solution with agitation. A clear aqueous solution containing 45 mg of the three 5β steriods and no precipitate will be present after standing for 24 hours.

Example XI

To make a formulation containing α ET, β ET and ED, the stock solution of hydroxypropyl-β-cyclodextrin is prepared as in Example III. 10 mg of α ET, 10 mg β ET, 10 mg of ED and 15 mg of DHEA will be added to 1 ml of the solution with agitation. A clear aqueous solution containing 45 mg of the DHEA and the three 5β steriods and no precipitate is present after standing for 24 hours.

The composition of matter according to the invention may be supplied as a dry powder or as a solution. If the composition of matter is to be injected into a subject it will be rendered sterile prior to injection. Accordingly, the composition of matter according to the invention may be supplied as a sterile cake, plug or powder or as a sterile lyophilized preparation in a sterile vial suitable for the addition of a sterile diluent, or as a sterile liquid solution in a sterile container.

The compositions of matter according to the invention may by supplied as a powder comprising the active pharmaceutical 5β steroid compound or compounds and amorphous cyclodextrin compound. If the composition is to be administered parenterally, for example iv, the composition of matter will be rendered sterile prior to such administration. Any of the several known means for rendering such pharmaceutical preparations sterile may be used so long as the active pharmaceutical compound is not inactivated and the complex with the amorphous cyclodextrin is not degraded. If the active pharmaceutical compound is heat stable, the composition of matter according to the invention may be heat sterilized. If the cytotoxic compound is not heat-stable but is not photo degraded the composition may be sterilized by exposure to ultraviolet light or by ionizing radiation. Alternatively, the composition of matter if in a powder form may be gas sterilized using for example ethylene oxide gas. In another alternative, the composition of matter according to the invention may be filter-sterilized using a 0.2 micron filter. If the composition of matter is an aqueous liquid, it may be filled in a sterile container and supplied as a sterile liquid ready for further dilution or injection neat. Alternatively such sterile liquids may be freeze-dried or lyophilized in a sterile container and capped.

In general the compositions of matter according to the invention will be made by dissolving the cyclodextrin in water and adding the 5β steroid compound to the aqueous cyclodextrin solution. Excipients, if any are desired, may be added with or subsequent to adding the 5β steroid compound. The resulting solution may be sterilized using any of the known methods appropriate to preserving the compound without significant degradation.

Preferably the solution will be sterile filtered, although other means such as terminal heat sterilization or irradiation may be employed as is known in the art, provided that the cyclodextrin compound is not significantly degraded. Alternatively, the components may be sterilized by any of the known methods appropriate to preserving the compound prior to mixing in water and may be mixed using sterile equipment and technique. The solution may be lyophilized in sterile containers and capped. Prior to use the lyophilized composition of matter may be reconstituted using sterile water for injection.

The container closure system used for containing the formulation according to the invention will also be treated to remove or destroy pyrogenic substances by means known in the art prior to filling and further processing. Thus the preferred compositions of matter according to the invention for parenteral administration, especially by the intravenous route will be nonpyrogenic. Nonpyrogenic preparations according to the invention, when administered to a subject, does not cause a febrile (basal body temperature raising) reaction. Although some bacterial endotoxin may be present, the amount is insufficient to elicit a febrile reaction. In general, such non-pyrogenic compositions will contain less than 10 U.S.P. bacterial endotoxin units per gram of product.

The formulation according to the invention may be supplied as a dry lyophilized powder as mentioned above or as a sterile non pyrogenic aqueous solution in a sterile container closure system such as a stoppered vial suitable for puncturing with a sterile syringe and needle.

Alternatively the formulation according to the invention may be supplied as a sterile non pyrogenic aqueous solution in a sterile syringe or syringe and needle. As a sterile solution or powder it may also include a pharmaceutically acceptable preservative. The formulation according to the invention may also be included in other dosage forms in addition to those appropriate for parenteral administration. Preferably, such other dosage forms will include one or more of the 5β steroids with or without DHEA. Such dosage forms may be in the form of aqueous suspensions, elixirs, or syrups suitable for oral administration, or compounded as a cream or ointment in a pharmaceutically acceptable topical base allowing the 5β steroid compounds with or without DHEA to be absorbed across the skin. In addition the formulation according to the invention may be compounded in a lozenge or suppository suitable for trans mucosal absorption.

The formulations according to the invention having been described herein may influence the ordinarily skilled artesian to make similar formulations using components that will be known in the art, without departing from the invention which is claimed herein:

We claim:

1. A composition of matter comprising at least one 5 β steroid and an amorphous cyclodextrin.

2. The composition of claim 1 wherein said 5β steroid is selected from the group consisting of α etiocholanolone, β etiocholanolone and etiocholandione.

3. The composition of claim 1 comprising etiocholandione and β etiocholanolone.

4. The composition of claim 1 comprising etiocholandione and a etiocholanolone.

5. The composition of claim 1 comprising etiocholandione, α etiocholanolone and β etiocholanolone.

6. The composition of claim 1 in a sterile aqueous solution suitable for parenteral administration.

7. The composition of claim 6 wherein said 5β steroid is selected from the group consisting of α etiocholanolone, β etiocholanolone and etiocholandione.

8. The composition of claim 6 comprising etiocholandione and β etiocholanolone.

9. The composition of claim 6 comprising etiocholandione and α etiocholanolone.

10. The composition of claim 6 comprising etiocholandione, α etiocholanolone and β etiocholanolone.

11. The composition of claim 6 wherein the composition is sterile and is contained within a sterile container.

12. The composition of claim 11 wherein the composition is non-pyrogenic when administered intravenously.

13. The composition of claim 12 herein said composition contains no more than 10 endotoxin units per gram.

14. The composition of claim 11 further comprising DHEA.

15. The composition of claim 14 wherein the composition is non-pyrogenic when administered intravenously.

16. The composition of claim 15 wherein said composition contains no more than 10 endotoxin units per gram.

17. The composition of claim 14 wherein said amorphous cyclodextrin has a degree of substitution of 2 to 7.

18. The composition of claim 6 wherein said amorphous cyclodextrin has a degree of substitution of 2 to 7.

19. The composition of claim 6 further comprising DHEA.

20. The composition of claim 1 wherein said amorphous cyclodextrin has a degree of substitution of 2 to 7.

21. A method for treating a condition selected from the group consisting of obesity, diabetes syndrome, diabetes-associated hypercorticoidism, combinations thereof, and anemic disorders comprising administering to a mammal in need of such treatment a composition comprising an obesity-, diabetes-, hypercorticoidism- or anemia- antagonistic amount of at least one 5 β steroid and an amorphous cyclodextrin.

22. The method of claim 21 wherein said 5β steroid is selected from the group consisting of α etiocholanolone, β etiocholanolone and etiocholandione.

23. The method of claim 22 herein said composition contains no more than 10 endotoxin units per gram.

24. The method of claim 21 wherein said 5β steroid comprises etiocholandione and β etiocholanolone.

25. The method of claim 21 wherein said 5 β steroid comprises etiocholandione and α etiocholanolone.

26. The method of claim 21 wherein said 5 β steroid comprises etiocholandione, α etiocholanolone and β etiocholanolone.

27. The method of claim 21 wherein said composition further comprises a sterile aqueous solution suitable for parenteral administration.

28. The method of claim 27 wherein said 5 β steroid is selected from the group consisting of α etiocholanolone, β etiocholanolone and etiocholandione.

29. The method of claim 27 wherein said 5 β steroid comprises etiocholandione and β etiocholanolone.

30. The method of claim 27 wherein said 5 β steroid comprises etiocholandione and α etiocholanolone.

31. The method of claim 27 wherein said 5 β steroid comprises etiocholandione, α etiocholanolone and β etiocholanolone.

32. The method of claim 27 wherein said composition is sterile and is contained within a sterile container.

33. The method of claim 32 further comprising DHEA.

34. The method of claim 33 wherein said composition is non-pyrogenic when administered intravenously.

35. The method of claim 34 wherein said composition contains no more than 10 endotoxin units per gram.

36. The method of claim 33 wherein said amorphous cyclodextrin has a degree of substitution of 2 to 7.

37. The composition of claim 27 wherein said amorphous cyclodextrin has a degree of substitution of 2 to 7.

38. The method of claim 27 further comprising DHEA.

39. The method of claim 21 wherein the said composition is non-pyrogenic when administered intravenously.

40. The method of claim 21 wherein said amorphous cyclodextrin has a degree of substitution of 2 to 7.

41. A method for treating a condition which responds to treatment with DHEA in a subject having blood comprising administering to the subject at least one 5 β steroid and DHEA in an amount that minimizes the contribution of the DHEA to the production of testosterone and estradiol while maximizing an amount of αET and βET circulating in the subject s blood from an initial dose administered to the subject.

42. The method of claim 41 wherein said at least one 5 β steroid and DHEA is in a formulation comprising an amorphous cyclodextrin wherein the formulation is suitable for parenteral administration.

43. The method of claim 42 wherein said formulation is non-pyrogenic.

* * * * *

UNITED STATES PATENT AND TRADEMARK OFFICE
CERTIFICATE OF CORRECTION

PATENT NO. : 5,824,668
DATED : October 20, 1998
INVENTOR(S) : Joseph Rubinfeld, Julius A. Vida, H. Leon Bradlow and Elliott L. Fineman It is certified that error appears in the above-identified patent and that said Letters Patent is hereby corrected as shown below:

Column 1, line 57 delete "Chrone's", insert --Crohn's--.

Column 2, line 40 delete "U.S. Pat. No. 4,353,793", insert --U.S. Pat. No. 4,352,793--.

Column 2, line 46 delete "{", insert --[--.

Column 2, line 51 delete "U.S. Pat. No. 4,474,881", insert --U.S. Pat. No. 4,474,811--.

Column 3, line 4 delete "hinokitol", insert --hinokitiol--.

Column 3, line 20 delete "Shimazu et al.", insert --Yamahira et al.--.

Column 3, line 28 delete "Shimazu et al.", insert --Yamahira et al.--.

Column 3, line 32 delete "U.S. Pat. No. 4,478,811", insert --U.S. Pat. No. 4,474,811--.

Column 3, line 60 delete "bacilli", insert --bucally--.

Column 4, lines 2 & 3 delete "trans-mucocele", insert --trans-mucosally--.

Column 5, line 33 delete "$\alpha$ ET", insert --$\alpha$ Etiocholanolone ($\alpha$ ET)--

Column 5, line 33 delete "$\beta$ ET", insert --$\beta$ Etiocholanolone ($\beta$ ET)--

Column 5, line 44 delete "ED", insert --Etiocholandione (ED)--.

UNITED STATES PATENT AND TRADEMARK OFFICE
CERTIFICATE OF CORRECTION

PATENT NO. : 5,824,668
DATED : October 20, 1998
INVENTOR(S) : Joseph Rubinfield, Julius A. Vida, H. Leon Bradlow and Elliott L. Fineman It is certified that error appears in the above-identified patent and that said Letters Patent is hereby corrected as shown below:

Column 5, line 63 delete "etiocholanolondione", insert --etiocholandione--.

Column 6, lines 26 & 27 delete "Zumoffet al.", insert --Zumoff et al.--.

Column 6, line 48 delete "5p", insert --5β--.

Column 10, line 66 delete "are", insert --is--.

Column 15, lines 14 & 15 delete "artesian", insert --artisan--.

Column 15, line 27 delete "a", insert --α--.

Column 15, line 45 delete "herein", insert --wherein--.

Column 16, line 10 delete "herein", insert --wherein--.

Signed and Sealed this

Eleventh Day of April, 2000

Attest:

Attesting Officer

Q. TODD DICKINSON

Director of Patents and Trademarks